United States Patent [19]

Agarwal

[11] Patent Number: 4,488,239
[45] Date of Patent: Dec. 11, 1984

[54] TEMPERATURE CONTROL SYSTEM FOR OLEFIN OXIDATION REACTOR

[75] Inventor: Suresh C. Agarwal, Euclid, Ohio

[73] Assignee: The Babcock & Wilcox Company, New Orleans, La.

[21] Appl. No.: 370,703

[22] Filed: Apr. 22, 1982

[51] Int. Cl.³ .............................................. G05D 7/00
[52] U.S. Cl. .................................... 364/500; 364/557; 422/62; 422/110
[58] Field of Search ............... 364/496, 500, 502, 557; 203/1; 436/55; 422/62, 105, 108, 110, 111; 260/700; 585/263, 401, 501, 950, 951

[56] References Cited

U.S. PATENT DOCUMENTS

| | | | |
|---|---|---|---|
| 3,080,219 | 3/1963 | Harvey, Jr. | 364/500 |
| 3,373,218 | 3/1968 | Schuman | 585/950 |
| 4,111,218 | 9/1978 | Hobbs | 203/1 |
| 4,132,529 | 1/1979 | Schwimmer | 436/55 |
| 4,132,530 | 1/1979 | Schwimmer | 364/500 |
| 4,187,542 | 2/1980 | Ball et al. | 364/502 |
| 4,236,219 | 11/1980 | Killebrew, Jr. et al. | 422/62 |
| 4,241,230 | 12/1980 | Drinkard | 422/62 |
| 4,249,908 | 2/1981 | Funk | 364/557 |
| 4,257,105 | 3/1981 | Stewart et al. | 364/501 |
| 4,329,150 | 5/1982 | Drinkard | 364/500 |

Primary Examiner—Raulfe B. Zache
Assistant Examiner—Dale M. Shaw
Attorney, Agent, or Firm—Vytas R. Matas; Robert J. Edwards

[57] ABSTRACT

A temperature control system controls the temperature of an olefin oxidation reactor by measuring various parameters in the reactor and in flow lines to and from the reactor, and using these parameters with known quantities for specific heat of the feed and effluent and heats of vaporization and reaction, to calculate a coolant flow rate set point. Parameters relating to the heat balance with regard to a desired olefin oxide product and undesired carbon dioxide products are utilized for correct control. Equipment is also provided for ascertaining the state of a catalyst used in the reaction.

2 Claims, 1 Drawing Figure

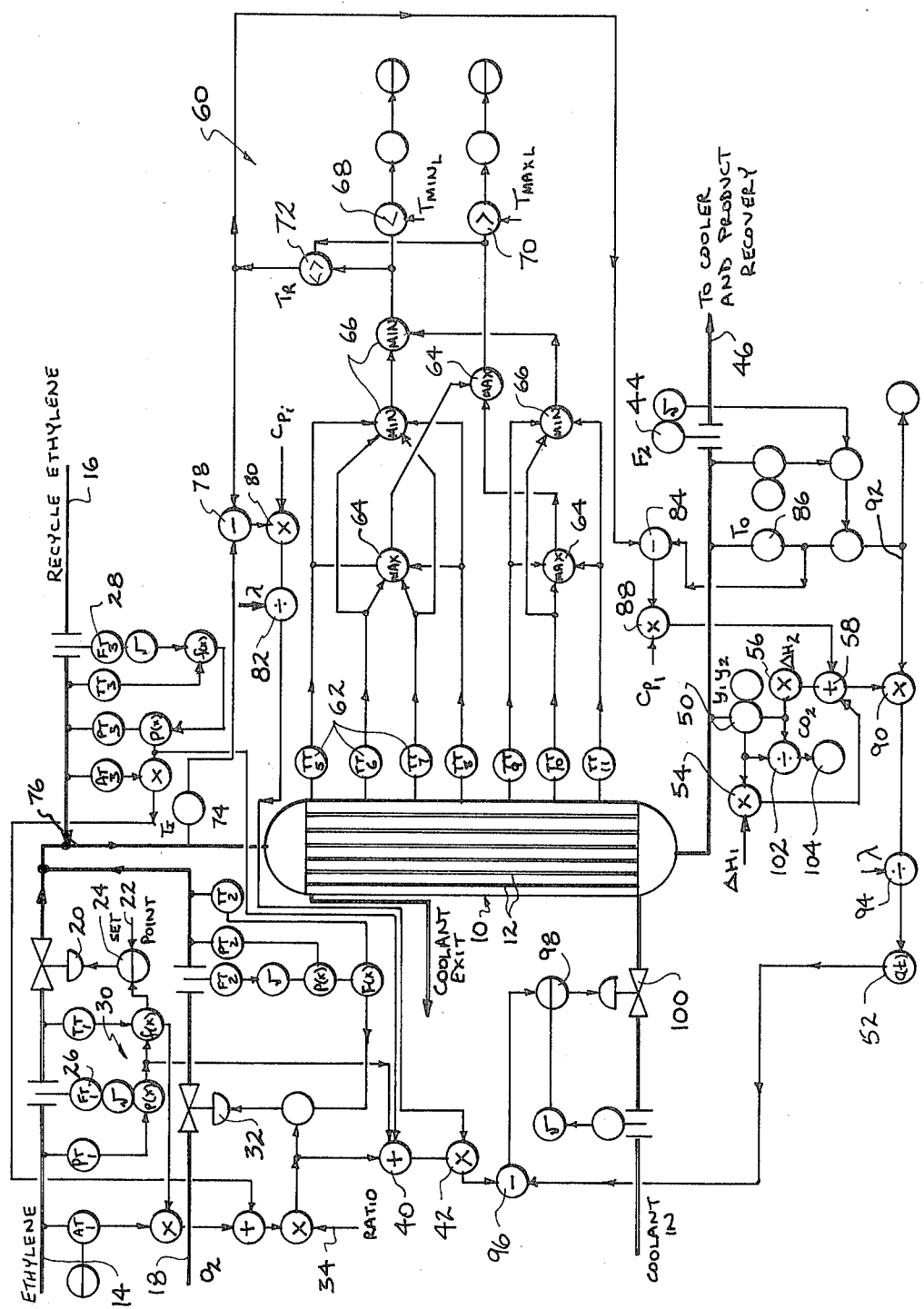

TEMPERATURE CONTROL SYSTEM FOR OLEFIN OXIDATION REACTOR

FIELD AND BACKGROUND OF THE INVENTION

The present invention relates, in general, to temperature control equipment techniques in chemical reactors and, in particular, to a new and useful temperature control system for an olefin oxidation reactor which regulates the rate of coolant flow to maintain the reactor temperature within a desired temperature range.

Various techniques and systems are known for controlling chemical reactors.

U.S. Pat. No. 3,080,219 to Harvey Jr. discloses a control system for a polymerization reactor. This system is applicable to stirred tank reactors where temperatures are uniform throughout the reactor due to mixing.

U.S. Pat. No. 4,132,530 to Schwimmer discloses a temperature control system for an exothermic or endothermic reaction. Schwimmer provides a plurality of temperature sensors distributed along the reactor axis for measuring maximum reactor temperatures used in a control scheme.

Other references which are relevant in understanding the present invention are: U.S. Pat. No. 3,373,218 to Schuman, U.S. Pat. No. 4,132,529 to Schwimmer, U.S. Pat. No. 4,187,542 to Ball et al. and U.S. Pat. No. 4,257,105 to Stewart et al. All these references disclose various control techniques for chemical reactors.

In an ethylene oxide manufacturing process, ethylene and oxygen or air is mixed and fed to an isothermal multitubular reactor. Ethylene is oxidized into ethylene oxide in the presence of a catalyst and carbon dioxide and water are produced as by-products. Reactor temperature control objectives are:

Operation at the most economical temperature;
Operation within a safe zone;
Maximum conversion to ethylene oxide while minimizing by-products;
Reduced consumption of coolant;
Avoidance or elimination of unsafe operation; and
Reduced operator attention.

Reactor temperature control is of key significance because of the following factors:

1. The most economical temperature for oxidation is one at which the highest conversion to ethylene oxide occurs rather than to by-products.
2. Catalyst selectivity increases as the reaction temperature is lowered while ethylene conversion increases with increasing reactor temperature. Thus, temperature requirements for high selectivity and high conversion are opposed. This results in a narrow temperature range for reactor operation.
3. Increase in reaction temperature produces two effects: (1) overall rate of ethylene oxidation increases, and (2) catalyst selectivity to ethylene oxide decreases such that relatively more ethylene is converted into carbon dioxide and water. Moreover, heat generation increases by the fact that more ethylene is oxidized and overall reaction becomes less selective. Consequently, increase in temperature may result in:
a reactor runaway condition;
catalyst poisoning;
increased coolant demand;
an unsafe operating situation; and/or
increased operator attention.

Hence, neither a temperature rise nor a temperature drop is desirable.

In the state of the art system, reactor temperature control system is based on manipulating coolant flow rate. Its set point is directly based upon average reactor temperature. These control schemes result in almost all the deficiencies described above.

SUMMARY OF THE INVENTION

An object of the present invention is to provide a control system and technique which accomplishes the objectives of operation of an olefin oxidation reactor at the most economical and safe temperature range, with regard to a maximum conversion of the olefin to the desired olefin oxide and a minimization of by-products.

Another object of the invention is to provide such a control system and technique, in particular for ethylene oxidation reactors.

Another object of the invention is to provide a control system and technique which is also applicable to other exothermic and endothermic reactors.

According to the invention, a system is provided which controls the rate of coolant flow in the chemical reactor according to an algorithm which incorporates various parameters including reactor feed and effluent flow rates, specific heat of reactants and products, reactor and effluent temperatures, coolant heat of evaporation, reactant and product concentration and heat of reactions for various reactions taking place in the reactor.

In addition, temperatures are taken at varied locations along the reactor length, for obtaining a maximum and a minimum value for temperatures within the reactor for establishing a desired reactor temperature range.

Accordingly, another objective of the invention is to provide a temperature control system and method for controlling an olefin oxidation reactor which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWING

The only FIGURE in the drawing is a schematic representation of the inventive control system used in combination with a tubular reactor.

DESCRIPTION OF THE PREFERRED EMBODIMENT

Referring to the drawing in particular, the invention embodied therein comprises a control system for controlling the rate of coolant flow into a tubular reactor generally designated 10 having tubes 12 for the passage of an ethylene plus oxygen mixture. The reactor is particularly adapted to oxidize ethylene into ethylene oxide with carbon dioxide and water as by-products.

In the following, an algorithm which is used to control the coolant flow into the reactor, according to the invention, is developed. The symbols used correspond to symbols used in the FIGURE for ease of understanding.

Let Q be the coolant flow rate and $\lambda$ be its heat of vaporization. Assuming that there is no superheating of coolant, we have:

total heat removed by coolant $= Q\lambda$.

Let:
$F_1$ = Reactor feed flow rate;
$x_i$ = Concentration of component i in the reactor feed, where i=1 for ethylene, i=2 for carbon dioxide i=3 for ethane and i=4 for oxygen;
$T_I$ = Feed temperature;
$T_{Ref}$ = Reference Temperature; and
$C_{Pi}$ = Specific heat of feed.

Therefore, $$\text{total enthalpy of feed} = F_1 C_{Pi}(T_i - T_{Ref}) \text{ where,} \quad (1)$$

$$C_{Pi} = \sum_{k=1}^{4} C_{pik} x_i$$

where, $C_{P_k}$ = specific heat of component $k$.

Let:
$F_2$ = Reactor effluent flow rate;
$y_j$ = Concentration of component j in reactor effluent, where j=1 for ethylene oxide, j=2 for $Co_2$, j=3 for ethylene, j=4 for water; and
$T_O$ = Reactor effluent temperature.

Then, by reaction stoichiometry:

$$y_2 = y_4. \quad (2)$$

With the assumption that other impurities are small, we have:

$$y_1 = 1.0 - y_2 - y_3 - y_4. \quad (3)$$

Ethylene oxide concentration may be either measured directly, or evaluated from equation (3).

Let:
$\Delta H_1$ = heat of reaction for ethylene oxidation into ethylene oxide; and
$\Delta H_2$ = heat of reaction for ethylene oxidation into carbon dioxide and water.

Then, heat generated in reactor
= heat of reaction (ethylene to ethylene oxide) + heat of reaction (ethylene to carbon dioxide)
= $F_2 Y_1 \Delta H_1 + F_2 y_2 \Delta H_2$.

Let $T_R$ = reaction temperature. The heat consumed in elevating feed to reaction temperature = $F_1 C_{Pi}(T_i - T_R)$.
Heat removed in cooling reaction products to reactor effluent temperature = $F_2 C_{P1}(T_R - T_O)$, where $$C_{P1} = \sum_{m=1}^{4} y_m C_{Pm}$$

For total heat balance:
heat removed by coolant = heat generated due to reaction + heat removed in cooling reaction products to reactor effluent temperature − heat used in heating feed to reaction temperature or:

$$Q\lambda = \quad (4)$$

$$F_2(y_1 \Delta H_1 + y_2 \Delta H_2) + F_2 C_{P1}(T_R - T_O) - F_1 C_{Pi}(T_R - T_I).$$

Thus:

$$Q = \frac{1}{\lambda} [F_2\{y_1 \Delta H_1 + y_2 \Delta H_2 + C_{P1}(T_R - T_O)\} - F_1 C_{Pi}(T_R = T_I)]$$

Equation (4) thus gives the desired coolant flow rate.

The invention, as shown in the FIGURE, presents a reactor control scheme based on the above analysis. The implementation shown herein is via a conventional electronic instrumentation and control system. The invention, however, can easily be implemented via a control computer system. Startup and shutdown controls, although not shown herein, can be easily added to this control scheme.

According to the invention, ethylene is provided over line 14, with recycled ethylene being provided over line 16. Oxygen or air is provided over line 18. The flow of ethylene over line 14 is controlled by a valve 20 which receives a desired set point value at 22. The set point value can also be modified in controller 24 by a feedback loop generally designated 30 which includes a flow rate transmitter 26. Line 16 for recycling ethylene also includes flow transmitter 28. The flow of oxygen or air is controlled over a valve 32 in accordance with a ratio set at 34 of oxygen to ethylene. The combined feed flow rates of ethylene $F_1$ are added in summing element 40 and provided to a multiplication element 42. The effluent flow rate $F_2$ is determined in a flow rate transmitter 44 connected to the effluent line 46. Effluent line 46 contains the desired product ethylene oxide plus carbon dioxide water, and unconverted ethylene. The concentration of ethylene oxide and carbon dioxide, $y_1$ and $y_2$, respectively, are obtained at a chromatography transmitter 50. The results of chromatography, that is, ethylene oxide and carbon dioxide concentration signals are used for determining the state of the catalyst. Ethylene oxide concentration signal is divided by carbon dioxide concentration signal is element 102 and displayed on a strip chart recorder 104. This element is useful to measure the state of the catalyst in the reactor, to determine whether the catalyst needs to be regenerated or replaced. The element can also be used in an emergency control for sounding an alarm and the like.

The carbon dioxide and ethylene oxide quantities are multiplied respectively by the heat of reaction for ethylene to carbon dioxide, $\Delta H_2$, and the heat of reaction for ethylene to ethylene oxide, $\Delta H_1$. These operations are accomplished in multiplication elements 54 and 56. The results of these two operations are added in adding element 58.

The maximum and minimum temperatures within the reactor are determined using a temperature sensing means generally designated 60. Temperature sensing means 60 comprises a plurality of individual or banks of temperature sensors 62 which are distributed along the length of reactor 10. Elements 64 are utilized to determine the maximum temperature among temperature sensors 62 and elements 66 are utilized to determine the minimum temperature among these sensors. Values for minimum and maximum temperature are applied by elements 68 and 70. The maximum and minimum temperatures are also processed in element 72 to yield a value $T_R$, the reaction temperature. A temperature sensor 74 is provided in the reactant input line 76 to sense the feed temperature $T_I$. This temperature is subtracted from the reactor temperature in subtracting element 78 which quantity is multiplied by the specific heat of the feed $C_{Pi}$ in multiplication element 80 and the result is divided by lamda in division element 82. The resultant factor is multiplied in multiplication element 42 by the flow feed quantity $F_1$.

The reactor temperature $T_I$ is also provided to subtraction element 84 where the effluent temperature $T_O$, as sensed by temperature transmitter 86, is subtracted therefrom. The result of the subtraction operation is multiplied by the specific heat quantity $C_{Pl}$ in multiplication element 88. The resultant is added in adding element 58 to the heater reaction components and the result of this operation is multipled in multiplication element 90 by the flow rate $F_2$ as supplied over line 92. The result of this operation is divided by lamda in division element 94. As mentioned above, the process time delay factor is considered in element 52. The subtraction element 96 is provided to subtract the input factors from the output factors to produce a coolant flow amount signal which is utilized in coolant flow controller 98 to control a coolant flow valve 100. Thus, according to the invention, the apparatus controls the temperature of an ethylene oxidation in a tubular reactor 10 by external cooling of the reactor tubes to which ethylene and oxygen/air are the feed streams and the reactor tubes contain catalyst.

Either maximum or minimum temperature, whichever is beyond the associated operating limit as selected in elements 68 and 70, is selected in element 72 for the computation of desired coolant flow rate to the reactor.

According to the invention, the coolant flow rate is calculated from heat input/output balance. Actual ethylene conversion to ethylene oxide in the reactor is measured by measuring the ethylene oxide concentration in the reactor stream over chromatography transmitter 50. Actual ethylene conversion to carbon dioxide as a side reaction is also measured by the transmitter 50. The results of the chromatography signal computation is compensated for process time delay by element 52 prior to determining the coolant flow rate set point as applied to controller 98. The control system generates a signal which is based on carbon dioxide and ethylene oxide concentrations.

According to the invention, the reactor temperature is maintained between a narrow operating limit wich is specified by the minimum and maximum operating temperature. In this way, ethylene conversion to ethylene oxide is maintained at an economical level as the specification of temperature limits is at least pseudo-optimal for a given catalyst, from the selectivity and conversion standpoint. Ethylene conversion to carbon dioxide is reduced as the reactor is operated within the temperature limit where catalyst selectivity toward carbon dioxide is minimal. Also, the reactor operation is within safety limits under all operating regimes, that is during start-up, shut-down and modulating control. The reactor operation is also within safe conditions for drastic variations in feed flow rate to the reactor.

The calculation of coolant flow rate set point in control 98 is based on ethylene conversion to carbon dioxide in addition, so that this provides for removing heat generated by the side reaction in addition to the heat generated by the desired reaction.

Additional indication signals are provided at chart recorder element 104 to display the state of the catalyst.

The control structure according to the invention is a feed forward arrangement for the desired coolant flow rate prediction and feedback for coolant flow control.

While a specific embodiment of the invention has been shown and described in detail to illustrate the application of the principles of the invention, it will be understood that the invention may be embodied otherwise without departing from such principles.

What is claimed is:

1. An arrangement for controlling the temperature of a reactor for containing a reaction from at least one reactant to at least one product, the reactor having a feed line for the reactant and an effluent line for the product, comprising:

a feed flow transmittter connected to the feed line for measuring the flow of reactant to the reactor;

an effluent flow transmitter connected to the effluent line for measuring the flow of product from the reactor;

a feed temperature sensor connected to the feed line for sensing the reactant temperature;

an effluent temperature sensor connected to the effluent line for measuring the product temperature;

reactor temperature sensing means connected to the reactor for measuring a temperature of reactor;

concentration sensing means connected to the effluent line for measuring the concentration of the at least one product in the effluent line;

a coolant flow line to the reactor for supplying coolant to the reactor at a coolant flow rate;

coolant flow rate control means in said coolant line; and circuit means connected to said feed and effluent flow transmitters, said feed and effluent temperature sensors and said reactor temperature and concentration sensing means, for generating a coolant flow signal, said circuit means connected to said coolant flow control means for controlling the flow of coolant to the reactor according to said coolant flow signal, said circuit means receiving quantities proportional to the heat of reaction for at least one reaction in the reactor, specific heats of the reactant and product, and the heat of vaporization of the coolant, said circuit means operable to subtract a quantity proportional to an amount of heat consumed in supplying reactant to the reactor from a quantity proportional to an amount of heat generated and lost in the reactor and effluent line and to divide the resulting quantity by the specific heat of the coolant to generate the coolant flow signal wherein said circuit means is operable to generate the coolant flow signal (Q) using the formula $$Q = \frac{1}{\lambda} [F_2 \{y_1 \Delta H_1 + y_2 \Delta H_2 + C_{Pl}(T_R - T_O)\} - F_I C_{Pi}(T_R - T_I)].$$

where:
Q = coolant flow rate signal
$\lambda$ = coolant heat of vaporization
$F_2$ = effluent flow rate
$y_1$ = a first product condensation
$\Delta H_1$ = heat of reaction of reactant to first product
$y_2$ = a second product concentration
$\Delta H_2$ = heat of reaction of reactant to second product
$C_{Pl}$ = specific heat of effluent
$T_R$ = reactor temperature
$T_O$ = effluent temperature
$F_1$ = feed flow rate $C_{Pi}$ = specific heat of feed $T_I$ = feed temperature wherein ethylene plus oxygen is supplied to the reactor as reactant and ethylene oxide plus carbon dioxide and water are generated as products, $y_1$ being the concentration of ethylene oxide, $y_2$ being the concentration of carbon dioxide, $H_1$ being the heat of reaction of ethylene plus oxygen to ethylene oxide, $H_2$ being the heat of reaction of ethylene plus oxygen to carbon dioxide.

2. An arrangement according to claim 1, wherein said reactor temperature sensing means comprises a plurality of temperature sensors distributed along the length of said reactor, and a minimizing/maximizing circuit connected to said temperature sensors for obtaining a minimum and a maximum temperature among said temperature sensors of the reactor.

* * * * *